United States Patent
Ekin et al.

(10) Patent No.: US 9,286,671 B2
(45) Date of Patent: Mar. 15, 2016

(54) METHOD FOR DETERMINING AT LEAST ONE APPLICABLE PATH OF MOVEMENT FOR AN OBJECT IN TISSUE

(75) Inventors: Ahmet Ekin, Eindhoven (NL); Hubert Cecile Francois Martens, Eindhoven (NL)

(73) Assignee: Medtronic Bakken Research Center B.V., Maastricht (NL)

(*) Notice: Subject to any disclaimer, the term of this patent is extended or adjusted under 35 U.S.C. 154(b) by 263 days.

(21) Appl. No.: 13/979,150

(22) PCT Filed: Jan. 13, 2012

(86) PCT No.: PCT/IB2012/050169
§ 371 (c)(1),
(2), (4) Date: Jul. 11, 2013

(87) PCT Pub. No.: WO2012/098485
PCT Pub. Date: Jul. 26, 2012

(65) Prior Publication Data
US 2013/0287280 A1 Oct. 31, 2013

(30) Foreign Application Priority Data
Jan. 20, 2011 (EP) .................................. 11151552

(51) Int. Cl.
*G06K 9/00* (2006.01)
*G06T 7/00* (2006.01)
(Continued)

(52) U.S. Cl.
CPC ........... *G06T 7/0012* (2013.01); *A61B 17/3403* (2013.01); *A61B 19/201* (2013.01);
(Continued)

(58) Field of Classification Search
None
See application file for complete search history.

(56) References Cited

U.S. PATENT DOCUMENTS 6,505,065 B1 * 1/2003 Yanof et al. ................... 600/427
6,671,538 B1 * 12/2003 Ehnholm ............... A61B 19/20
382/131

(Continued)

FOREIGN PATENT DOCUMENTS

WO WO2009134820 11/2009

OTHER PUBLICATIONS

Shamir et al. "Trajectory planning method for reduced patient risk in image-guided neurosurgery: concept and preliminary results," Proc. SPIE 7625, Medical Imaging 2010: Visualization, Image-Guided Procedures, and Modeling, 762501, pp. 1-8.*

(Continued)

*Primary Examiner* — Vu Le
*Assistant Examiner* — Samah Beg
(74) *Attorney, Agent, or Firm* — Harness, Dickey & Pierce, PLC

(57) ABSTRACT

A method for determining an applicable path of movement of an object in human or animal tissue is based on intensity data obtained by a 3D imaging technique. The applicable path of movement connects a starling position of the object with a defined target location. The method includes defining the target location of a reference point of the object and choosing at least one possible starting position of the reference point of the object. Further, the method includes determining a candidate path of movement between the corresponding possible starling position and the defined target location. Next, the candidate path of movement is evaluated for being an applicable path. The candidate path is evaluated based on information about local intensity extrema and/or intensity variation resulting from the intensity data along the candidate path of movement.

20 Claims, 4 Drawing Sheets

(51) Int. Cl.
*A61B 17/34* (2006.01)
*A61B 19/00* (2006.01)
*G06T 15/08* (2011.01)
*G06F 19/00* (2011.01)

(52) U.S. Cl.
CPC .......... *A61B 19/50* (2013.01); *G06F 19/3437* (2013.01); *G06T 15/08* (2013.01); *A61B 2019/507* (2013.01); *G06F 19/321* (2013.01); *G06F 19/345* (2013.01); *G06T 2207/10088* (2013.01); *G06T 2207/30016* (2013.01); *G06T 2207/30241* (2013.01)

(56) References Cited

U.S. PATENT DOCUMENTS

| | | | | |
|---|---|---|---|---|
| 2002/0156365 | A1* | 10/2002 | Tsekos | 600/411 |
| 2003/0068074 | A1 | 4/2003 | Hahn | |
| 2003/0220557 | A1* | 11/2003 | Cleary et al. | 600/409 |
| 2004/0249809 | A1* | 12/2004 | Ramani et al. | 707/4 |
| 2007/0167727 | A1 | 7/2007 | Menezes et al. | |
| 2008/0082110 | A1* | 4/2008 | Rodriguez Ponce | 606/130 |
| 2008/0123922 | A1 | 5/2008 | Gielen et al. | |
| 2008/0160489 | A1* | 7/2008 | Bruijns | 434/272 |
| 2009/0070143 | A1* | 3/2009 | Haider | 705/3 |
| 2009/0171184 | A1* | 7/2009 | Jenkins et al. | 600/411 |
| 2010/0121151 | A1* | 5/2010 | Donhowe | A61B 1/00009 600/141 |
| 2011/0007071 | A1 | 1/2011 | Pfister | |
| 2012/0203530 | A1* | 8/2012 | Sharma et al. | 703/9 |
| 2013/0085344 | A1* | 4/2013 | Merkl et al. | 600/300 |
| 2014/0344742 | A1* | 11/2014 | Wiemker et al. | 715/771 |
| 2015/0230875 | A1* | 8/2015 | Shademan | A61B 19/50 600/407 |

OTHER PUBLICATIONS

Vaillant et al. "A Path-Planning Algorithm for Image-Guided Neurosurgery", 1997, pp. 467-476.*
Shamir et al. "Reduced risk trajectory planning in image-guided keyhole neurosurgery," Medical Physics 39(5), May 2012, pp. 2885-2895.*
Liu et al. "A Surgeon Specific Automatic Path Planning Algorithm for Deep Brain Stimulation," Proc. SPIE 8316, 83161D (2012).*
Beriault et al. "A multi-modal approach to computer-assisted deep brain stimulation trajectory planning", Int J CARS (2012) 7: pp. 687-704.*
Essert et al. "Automatic computation of electrode trajectories for Deep Brain Stimulation: a hybrid symbolic and numerical approach", Int J CARS (2012) 7: pp. 517-532.*
Liu et al. "Multisurgeon, Multisite Validation of a Trajectory Planning Algorithm for Deep Brain Stimulation Procedures", IEEE Transactions on Biomedical Engineering, vol. 61, No. 9, Sep. 2014, pp. 2479-2487.*
J.D. Johansson et al., "Simulation of Reflected Light intensity changes During Navigation and Radio Frequency Lesioning in the Brain", Journal of Biomedical Optics, 14, 2007. pp. 1-21.

* cited by examiner

METHOD FOR DETERMINING AT LEAST ONE APPLICABLE PATH OF MOVEMENT FOR AN OBJECT IN TISSUE

FIELD OF THE INVENTION

The invention relates to a method for determining at least one applicable path for the movement of an object, especially of a surgical and/or diagnostical device, in human tissue or animal tissue by means of a data set of intensity data obtained by a 3D imaging technique, the path of movement connecting a starting position of the device with a defined target location. The invention also relates to a computer-readable medium such as a storage device a floppy disk, CD, DVD, Blue Ray disk, or a random access memory (RAM), as well as a computer program product comprising a computer usable medium including computer usable program code and a computerized system.

BACKGROUND OF THE INVENTION

Healthcare diagnosis decision support systems or computer-aided diagnosis or computer-assisted diagnosis (CAD) systems are used in medicine to assist users like medical experts or physicians in the interpretation of medical images. Imaging techniques in X-ray, magnetic resonance imaging (MRI), and Ultrasound diagnostics yield a great deal of information, which the user has to analyze and evaluate comprehensively in a short time. CAD systems help scan digital images, e.g. from magnetic resonance imaging, for typical appearances and to highlight conspicuous structures, such as vessels, nerve pathways, ventricles, functionally eloquent regions and/or tumor regions. Usually, machine-learning technologies, such as a decision tree and neural network, are utilized to build classifiers based on a large number of known cases with ground truth, i.e., cases for which the diagnosis has been confirmed by pathology. The classifier bases its diagnosis on a computational structure built from known cases and inputted features for the unknown structure case. The classifier output indicates the estimated nature of the unknown structure and optionally a confidence value. As the precision of medical imaging facilities improves to detect very small structures, and as the number of digital images to be processed increases this type of CAD becomes increasingly important as a tool to assist users like physicians. The computer-produced classification is considered a second opinion to a user like a physician in order to raise the accuracy and confidence associated with diagnosis.

Computer assisted surgery (CAS) represents a surgical concept and set of methods, that use computer technology for presurgical planning, and for guiding or performing surgical interventions. CAS is also known as computer aided surgery, computer assisted intervention, image guided surgery and surgical navigation, but these terms that are more or less synonyms with CAS.

The traditional approach of determining an applicable path of movement for a surgical and/or diagnostical device (a safe surgical trajectory) in an image guided therapy like MRI always comprises the two basic steps of: segmenting each critical structure in a spatial region defining the possible path(s) of movement around these regions and afterwards determining a corresponding safe or applicable path. One important area of application is brain surgery. In detail, the traditional surgery planning mainly follows the following steps:

In a first step, the target location is defined manually, or automatically, or in a semi-automated manner. This either involves registering the magnetic resonance (MR) volume to a template, often in the stereotactic coordinate system, and detection of anatomical structures from this transformation, or identifying some point and plane landmarks, such as Mid-sagittal plane, and AC/PC points to determine the location of the target. Once the target is determined, the planning reduces to the detection of an entry point. In many cases, the path between the entry and target points has to be straight and should not hit the critical structures.

The second step is the identification of critical structures, such as vessels, gyri and sulci, ventricles, and some functionally eloquent regions in the brain. This involves segmenting these structures for example from contrast-enhanced $T_1$ weighted MR images by applying a set of image segmentation algorithms. Functionally eloquent regions are determined by analyzing fMRI (functional Magnetic Resonance images) and/or DTI (diffusion tensor images) data.

SUMMARY OF THE INVENTION

It is an object of the invention to provide an enhanced method and an enhanced system for determining at least one applicable path of movement for a surgical and/or diagnostical device in tissue by means of a data set obtained by a 3D imaging technique.

This object is achieved by the present invention as defined in the independent claims.

The method according to the invention comprises the steps: (i) defining the target location of a reference point of the device and choosing at least one possible starting position of the reference point of the device; (ii) determining a candidate path of movement between the corresponding possible starting position and the defined target location; and (iii) evaluating the candidate path of movement as being an applicable path depending on information about local intensity extrema and/or intensity variation resulting from the intensity data along the candidate path of movement.

Instead of the earlier mentioned two-step surgery planning approach of first determining the critical structures to avoid by segmenting them in multiple steps, and then determining the applicable path of movement (the safe trajectory) as a function of these segmentation results, a direct search for the applicable path of movement by skipping the segmentation step is performed in the method according to the invention. In other words, the method according to the invention does not consider the position and extension of critical structures as a whole, but simply looks for information about the intensity maxima and/or intensity minima and/or intensity variation (intensity information) resulting from the intensity data along the candidate path of movement indicating the presence of a critical structure in a domain of the candidate path. The critical structures are structures within the tissue, such as vessels, nerve pathways, ventricles, and/or functionally eloquent regions. The information about the intensity extrema and/or intensity variation of the data set is therefore directly used to determine at least one applicable path of movement. The method according to the invention has inter alia the following advantages:

direct evaluation of path candidates by intensity characteristics without need for segmentation process;

automatic adaptation to local intensity characteristics thereby avoiding the intensity inhomogeneity problems affecting e.g. MR images;

flexibility to add other types of constraints, such as integration of functional information, in the searching step of determining the possible path(s) of movement, and support for non-straight paths by extending the method to a search for multiple line segments;

option for providing an explanatory display of the path information as intensity plots and image-based thumbnails.

To determine the safety level of a candidate path, an intensity profile along the possible path of movement based on the information about the intensity extrema and/or intensity variation is analyzed. A safe or applicable path must not have large maxima or large minima in the path region. These maxima and/or minima are detected by a so called sliding window approach, where for each point, a window is centered and the maximum and the minimum intensity within the window are computed. If the center pixel is either the maximum or the minimum, it can be a critical structure. To verify this, the difference of the maximum and the minimum in the window is compared with the intensity at the target location to determine the saliency of the peak and valley. Afterwards, considering some spatial constraints, the trajectory is determined to be safe or not. A candidate path determined as safe is an applicable path.

According to a preferred embodiment of the invention, the candidate path of movement is a linear path of movement connecting the starting position and the target location along the shortest route. The linear path of movement is the most widely used type of path. A typical surgical and/or diagnostical device using a linear path is a needle shaped or rod shaped device.

According to another preferred embodiment of the invention, the evaluation considers an expert assessment of the intensity data in an area around the candidate path of movement. The expert assessment preferably is a case-by-case decision of an expert whether an intensity variation or a local maximum (peak) or a local minimum (valley) results from a critical structure. With respect to the present invention, the term "expert" therefore relates to a person having the knowledge to interpret intensity data with reference to the displayed structures.

According to yet another preferred embodiment of the invention, the evaluation of the candidate path of movement is an automatic evaluation performed by a computerized system. This computerized system preferably is a CAD (computer-assisted diagnosis) or CAS (computer assisted surgery) system.

Preferably, the expert assessment together with the corresponding information about the intensity and/or intensity variation is used for a training (teaching) of the computerized system. The computerized system uses an adaptive algorithm to the intensity variations by learning the dynamic range of the intensity of the input data. The corresponding computerized system is based on a machine-learning technology, such as a decision tree, a support vector machine, adaboost, or a neural network. The classifier of this system bases its diagnosis on a computational structure built from known cases and inputted intensity extrema and/or intensity variation along the candidate path of movement.

The 3D imaging technique preferably is a medical imaging technique to generate a three-dimensional image of the inside of an object from a large series of two-dimensional X-ray images taken around a single axis of rotation. The 3D imaging technique is for example an X-ray computed tomography (CT) technique or an imaging ultrasound technique. According to a preferred embodiment of the invention the 3D imaging technique is a magnetic resonance imaging (MRI) technique, a nuclear magnetic resonance imaging (NMRI) technique, or a magnetic resonance tomography (MRT) technique. The intensity data are derived from $T_1$-weighted MR scans and/or $T_2$-weighted MR scans and/or $T^*_2$-weighted MR scans and/or by magnetization transfer MRI and/or by fluid attenuated inversion recovery (FLAIR) and/or by magnetic resonance angiography and/or by magnetic resonance gated intracranial CSF dynamics (MR-GILD).

According to a preferred embodiment of the invention, the human or animal tissue is brain tissue. An important application of the path determining method is brain surgery planning with the corresponding tissue being brain tissue. The critical structures within this tissue are vessels, gyri and sulci, ventricles, and/or functionally eloquent regions.

In a first alternative, allowable yaw and pitch angles of the allowable path are determined. The selected angles satisfy the two constraints: 1) the starting position should be on the same hemisphere as the target location, and 2) the search should be towards the top of the brain rather than to the sides or below the target location. Having determined the yaw and pitch angles, within that preset angle range, rays from the target location towards the surface of the brain are casted where potential starting positions are located. Finally, the intensity profile of each candidate path (candidate trajectory) is analyzed and labeled as safe or not, and/or given a continuous safety value. A candidate path labeled as safe or having a corresponding safety value is an applicable path.

In a second approach, a slice in the axial direction that corresponds to the top of the head (immediately satisfying the constraint that the search should be towards the top of the brain rather than to the sides or below the target location) is determined. For a target location on the left side of the brain, we choose the left half of the slice, and for a target location on the right, only the region of the slice corresponding to the right brain hemisphere is chosen (satisfying the constraint that the starting position should be on the same hemisphere as the target location). After that, the lines between each eligible point on the slice and the predetermined target location as described above form the candidate paths.

According to another embodiment of the invention, the method comprises the further step of displaying the at least one candidate path of movement or at least the starting position of the at least one candidate path of movement. In a preferred mode of graphic representation of the possible starting positions, a region of interest of possible starting position(s) is/are displayed, wherein the starting position(s) of applicable paths is/are displayed in a first color and the starting position(s) of the other paths is/are displayed in a second color. Especially, this can be in the form of a colored cortical surface map, where, for example, the first color is green, indicating applicable paths that satisfy the constraints of avoiding critical structures and the second color is red, indicating the other (unsafe) starting positions. If the tissue is brain tissue, the colored cortical surface map displays candidate entry positions on the skull.

Preferably, the candidate path of movement is displayed as an intensity profile. More preferably, the intensity profile is displayed in association with at least one image of an area around the local extrema, e.g. as a thumbnail image.

According to another preferred embodiment of the invention, an acceptance threshold of the information about the local intensity extrema and/or intensity variation for a given candidate path is determined or at least in part determined by the adjacent paths of said given candidate path.

According to another aspect of the present invention, the intensity profile is calculated by integrating the intensity data over the maximum cross section of the device perpendicular to a direction of motion along the candidate path of movement. This integration may be implemented in various ways. In one embodiment, the intensity value that results in the largest intensity change along the path is used to represent the cross-section. In another embodiment, multiple paths are considered separately to decide the safety of each individual path. Afterwards, the safety of the cross-section is computed as the aggregate of all single paths.

According to another aspect of the invention, a cross section can be defined to refer to a safety margin (defined as the distance to the nearest critical structure) around a candidate path. Within the pre-defined cross sectional area, no critical structure indicated by certain intensity characteristics exists.

In another aspect of the invention, all candidate paths are evaluated as safe or not. Afterwards, for each path, a safety margin is computed by detecting the closest path that are labeled as unsafe. Then, for the safe paths, the entry points on the surface of the brain can be color coded as a function of the computed safety margin. For the unsafe paths, a distinct color coding can be used that can be a function of the total number of intensity minima and maxima along the path, or a color coding scheme that discriminate whether only intensity minima, or intensity maxima or both are observable along the path.

The invention further relates to a computer-readable medium such as a storage device, a floppy disk, CD, DVD, Blue Ray disk, or a random access memory (RAM), containing a set of instruction that causes a computer to perform an aforementioned method and a computer program product comprising a computer usable medium including computer usable program code, wherein the computer usable program code is adapted to execute the aforementioned method.

The invention finally relates to a computerized system comprising a processing unit, a memory, a data interface, a display and an input device, wherein the system is adapted for performing the aforementioned method. Preferably the computerized system is a CAD (computer-assisted diagnosis) or CAS (computer assisted surgery) system.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
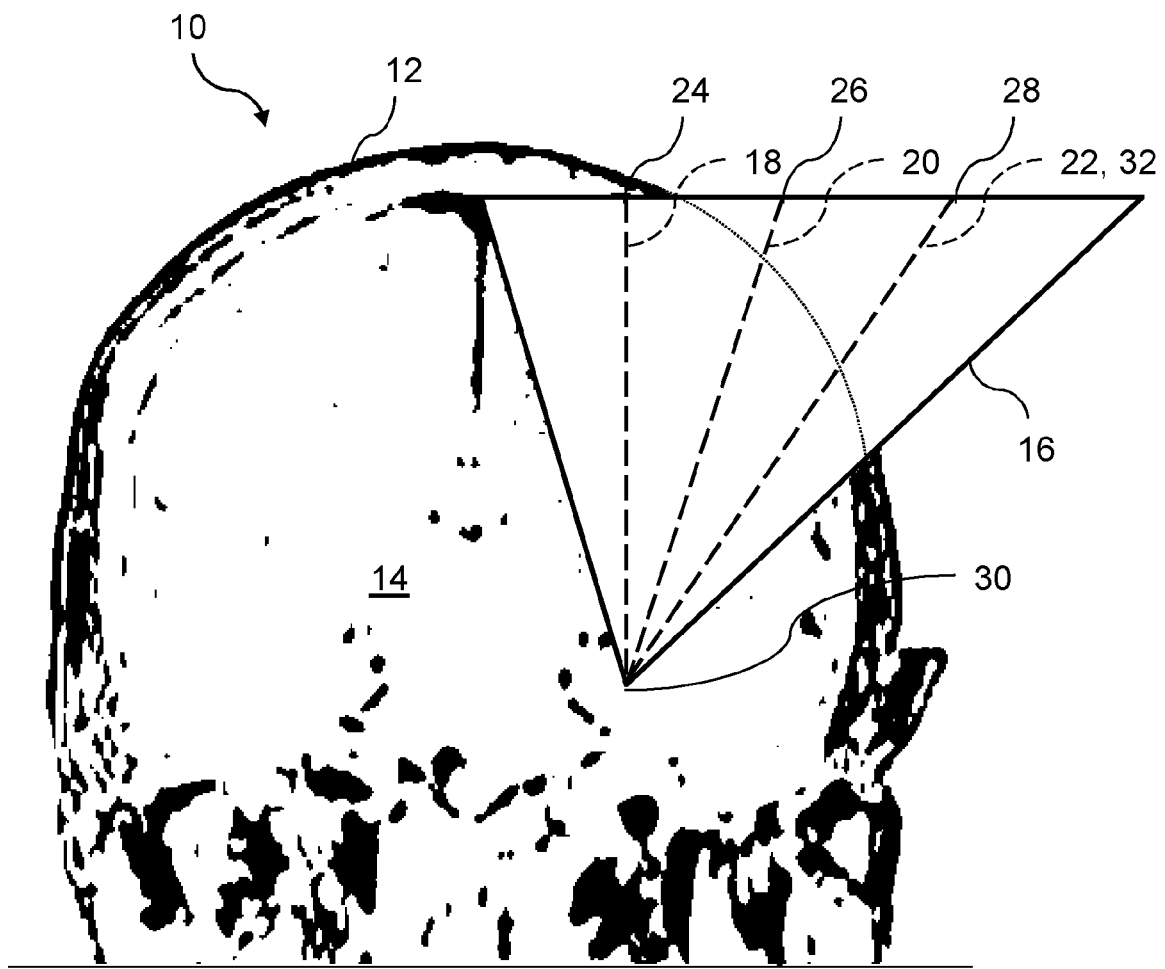
FIG. 1 shows a search region view from a coronal slice of a human head. A region of possible paths of movement is constructed by many possible paths (three of them explicitly shown) connecting corresponding starting positions with a common target location.

FIG. 1 shows a search region view from a coronal slice of a human head 10. The image shows the top of the skull 12 and the tissue 14 of the brain inside the skull 12. A region of candidate paths 16 for the movement of an object like a surgical or diagnostic device (not shown) in the brain tissue 14 is constructed by many candidate paths 18, 20, 22 (three of them explicitly shown) connecting corresponding possible starting positions 24, 26, 28 with a common target location 30.

An applicable path 32 for the movement of the device in tissue 14 is determined by means of a data set of intensity data obtained by the 3D magnetic resonance imaging technique, the applicable path 32 of movement is connecting a starting position 28 of the device with a defined target location 30. The corresponding determination method comprises the steps:

defining the target location 30 of a reference point of the device and choosing at least one possible starting position 24, 26, 28 of the reference point of the device;

determining the at least one candidate path of movement 18, 20, 22 between the corresponding possible starting position 24, 26, 28 and the defined common target location 30; and evaluating the candidate path of movement 18, 20, 22 as being the applicable path 32 depending on information about the local intensity minima/maxima (extrema) and/or intensity variation resulting from the intensity data along the candidate path of movement 18, 20, 22.

Figure 3:
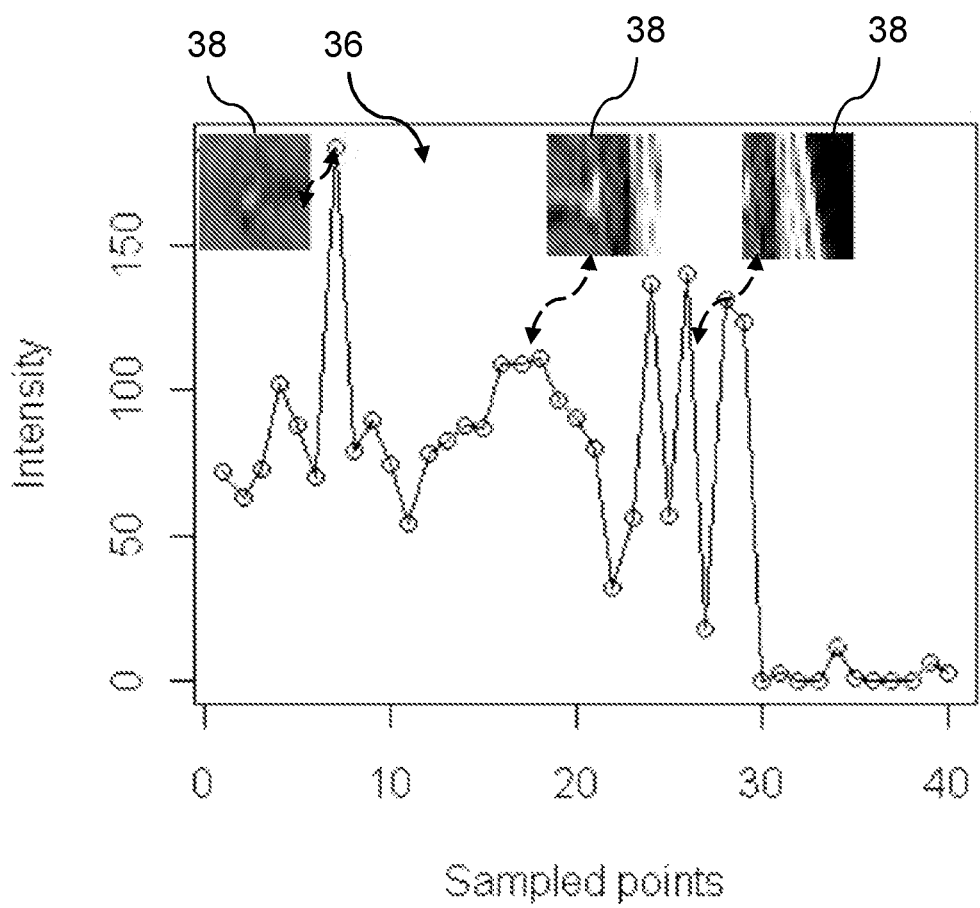
FIG. 3 the intensity profile of an "unsafe" possible path of movement.

The applicable path 32 for the movement of the device in the tissue 14 is a safe path which does not interfere with a critical structure (depicted in the insets of FIG. 3).

To determine the safety level of a candidate path 18, 20, 22, an intensity profile 34, 36 (shown in FIGS. 2 and 3) along the candidate path of movement 18, 20, 22 based on the information about the intensity extrema and/or intensity variation is analyzed. A safe applicable path 32 must not have large maxima or large minima in the (brain) tissue region. In general there are various options to define the feature "large".

A preferred approach for detecting these kind of maxima and/or minima is a sliding window approach. In a sliding window approach for each point or voxel (volume element represented by the point), a window is centered and the maximum and the minimum intensity within the window are computed to make sure that the corresponding point/voxel needs to be locally maximum or minimum to be a global maximum or minimum. Afterwards, any combination of the following steps can be done:

the absolute difference between the intensity of the current point or voxel and the intensity of the target location 30 should be within K* intensity standard deviation of the whole tissue (e.g. the brain volume). Factor K can be specified individually (e.g. K=1) and defines an upper and a lower intensity threshold. The current point or voxel is a large minimum if the intensity of this point/voxel is lower than the lower intensity threshold and a large maximum if higher than the upper intensity threshold.

X,y,z gradient of a volume surrounding the current point/voxel is computed by taking the x,y,z derivatives, respectively. From the derivatives, gradient magnitude is computed for each point/voxel. Then, a histogram is built from gradient magnitudes. Some percentile (e.g. P=80%) of the histogram is computed and assigned as threshold value. The above absolute difference between the intensity of the current point/voxel and the intensity at the target location 30 is compared with this threshold value to find the minimum or maximum.

The target location 30 is given initially (or found elsewhere) and the search for possible starting position 24, 26, 28 starts from this target location 30. As such, the intensity value at the target location 30 is already known and can be used for the detection of the minima and maxima.

If the pixel/voxel is either the maximum or the minimum, it indicates a critical structure. Afterwards, considering some spatial constraints, the candidate paths 18, 20, 22 are determined to be safe or not. The candidate path of movement 22 determined as safe is the applicable path 32. The critical structures within the shown brain tissue are vessels, gyri and sulci, ventricles, and/or functionally eloquent regions.

In a first alternative, allowable yaw and pitch angles of the applicable path 32 are determined. The selected angles satisfy the two constraints: 1) the starting position should be on the same hemisphere as the target location 30, and 2) the search should be towards the top of the brain rather than to the sides or below the target location 30. Having determined the yaw and pitch angles, within that preset angle range, rays from the target location 30 towards the surface of the brain are casted where the possible starting positions 24, 26, 28 are located. Finally, the intensity profile of each candidate path (candidate trajectory) 18, 20, 22 is analyzed and labeled as safe or not, and/or given a continuous safety value. A candidate path 18, 20, 22 labeled as safe or having a corresponding safety value is an applicable path 32.

In a second approach, a slice in the axial direction that corresponds to the top of the head (immediately satisfying the constraint that the search should be towards the top of the brain rather than to the sides or below the target location) is determined. For a target location 30 on the left side of the brain, the left half of the slice is chosen, and for a target location 30 on the right, only the region of the slice corresponding to the right brain hemisphere is chosen (satisfying the constraint that the starting position should be on the same hemisphere as the target location). After that, the lines between each eligible point on the slice and the predetermined target location 30 as described above form the candidate paths 18, 20, 22.

Figure 2:
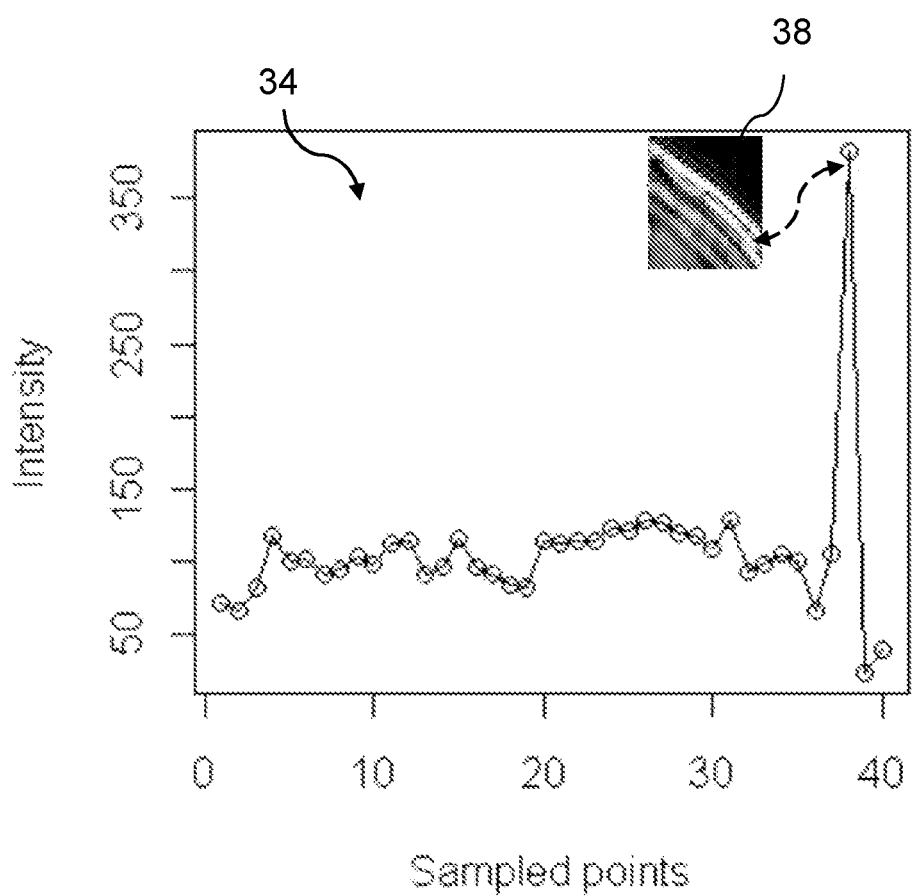
FIG. 2 the intensity profile of a "safe" possible path of movement therefore being an applicable path of movement.

FIG. 2 depicts the intensity profile 34 of a safe candidate path of movement 22; FIG. 3 depicts the intensity profile 36 of an unsafe candidate path of movement 20. The corresponding path of both intensity profiles start at the target location 30. The intensity profile 34 in FIG. 2 does not show large fluctuations (large minima or large maxima outside the intensity thresholds given by K* intensity standard deviation around the intensity of the target location 30) in the intensity until the end of the path, where there is a salient maximum in the intensity profile 34. This is expected as it corresponds to the intensity of the skull 12 and not the brain tissue. As a result, this candidate path 22 is labeled as safe. The candidate path of FIG. 3 has peaks (local maxima) within the brain region; therefore, it is considered as unsafe. Only the safe candidate path of movement 22 corresponding to the intensity profile 34 shown in FIG. 2 is an applicable path 32.

A further aspect of the method is an enhanced visualization strategy. In addition to the intensity profiles 34, 36, the user can also see an image 38 (a thumbnail image) of an area around the local maxima or local minima by clicking on the graphs as shown in FIGS. 2 and 3. In both Figures, only maxima are associated with a thumbnail image; however, both maxima and minima can be visualized in the same way. Furthermore, one can enlarge the size of the thumbnail image to get more information on the spatial context.

In another embodiment, one can add non-intensity constraints to the searched trajectories. This can be in the form of defining a search region as explained in the candidate entry point detection step. A search region can also be defined by using the result of another method in the form of a map that defines allowable and unacceptable points. This map can be generated from the analysis of a different modality, such as fMRI, DTI, $T_2$ etc. It can also be generated from the same MR $T_1$ contrast used for trajectory analysis. For example, one can use the result of cortical segmentation and brain mask for constraining the search area for the safe trajectory detection.

Figure 4:
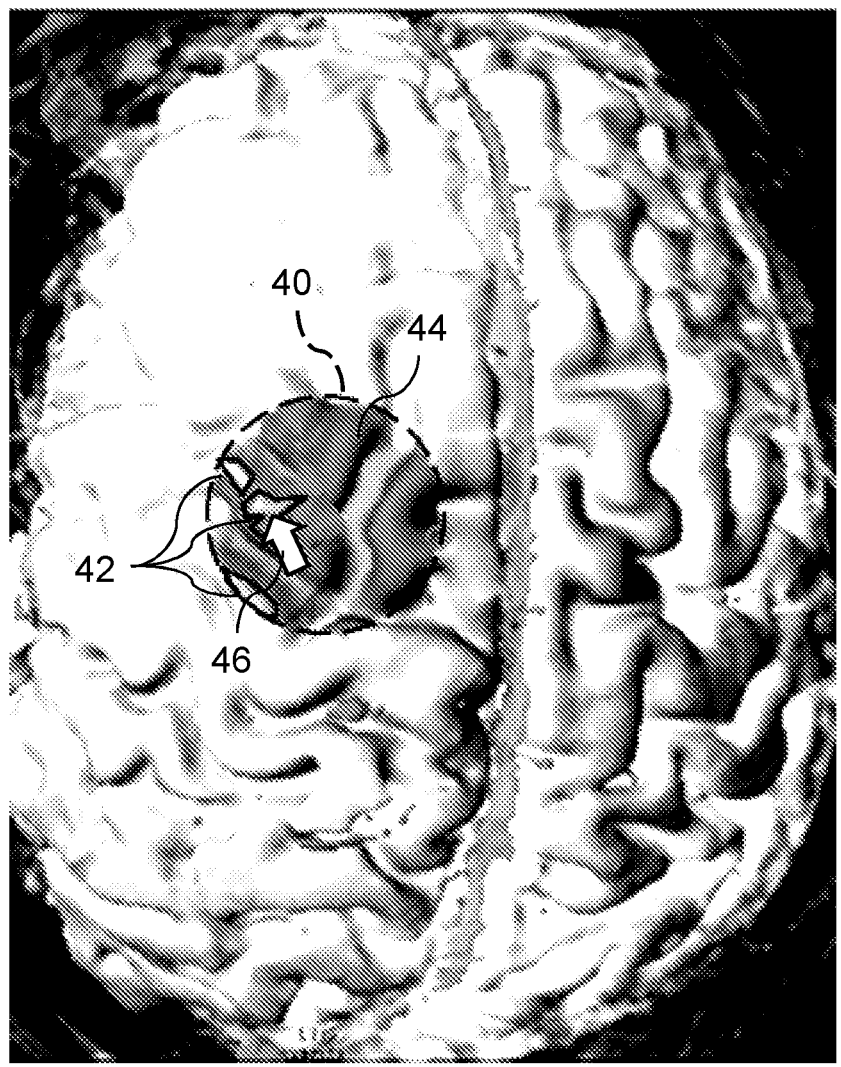
FIG. 4 a top view on the brain with a visualization of the region of possible paths subdivided into applicable paths and unsafe paths.

FIG. 4 shows a top view on the brain with a visualization of a region of interest 40 consisting of possible starting positions 24, 26, 28 of the candidate paths 18, 20, 22 within the region of candidate paths 16, the region of interest 40 subdivided into areas 42 of possible starting positions 28 of applicable paths 32 and a remaining area 44 of unsafe candidate paths 18, 20.

A user of a corresponding computer system like for example a surgeon can have a view of the brain on a display of the system depicting the region of interest (ROI) 40 of possible starting positions 24, 26, 28 comprising areas 42 colored green to indicate starting positions 28 of save applicable paths 32 and another area 44 colored red to indicate starting positions 24, 26 of unsafe paths.

If the user places the cursor 46 on a possible starting position, the corresponding intensity plot (as shown in FIGS. 2 and 3, is shown in one embodiment of the invention. In the example shown in FIG. 4, the cursor 46 points at one of the areas 42 of possible starting positions 28 of applicable paths 32. The system would depict the corresponding intensity profile of a "safe" applicable path of movement 32 like shown in FIG. 2. In a computer system being a computer assisted surgery (CAS) system, the cursor 46 will follow the movement of the surgical and/or diagnostical device.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for determining an applicable path of a movement of an object in a tissue based on intensity data obtained by a 3D imaging technique, the applicable path of movement connecting a starting position of the object with a defined target location, the method comprising acts of:
   defining the defined target location of a reference point of the object and choosing at least one possible starting position of the reference point of the object;
   determining a candidate path of movement between each position of the at least one possible starting position and the defined target location;
   directly after the determining act, evaluating the candidate path of movement as being an applicable path depending on information about local intensity extrema and/or intensity variation resulting from the intensity data along each candidate path of movement, wherein the evaluating act is performed on an unsegmented image of the tissue and forms an output including the applicable path; and
   rendering the output on a rendering device.

2. The method according to claim 1, wherein the candidate path of movement is a linear path of movement connecting the at least one possible starting position and the target location along a shortest route.

3. The method according to claim 1, wherein the evaluating act comprises an expert assessment of the intensity data in an area around each candidate path of movement.

4. The method according to claim 3, wherein the evaluating act is an automatic evaluation performed by a computerized system.

5. The method according to claim 4, wherein the expert assessment together with the information about the local intensity extrema and/or intensity variation is used for a training of the computerized system.

6. The method according to claim 1, wherein the 3D imaging technique is one of a magnetic resonance imaging technique, a nuclear magnetic resonance imaging technique, and a magnetic resonance tomography technique.

7. The method according to claim 1, wherein the rendering device is a display and the rendering act comprises displaying on the display at least one of the candidate path and the at least one possible starting position of the candidate path.

8. The method according to claim 1, wherein the rendering device is a display and the rendering act comprises displaying on the display a region of interest of the at least one possible starting position, wherein the at least one starting position of the applicable path is displayed in a first color and the at least one starting position of each candidate path not being the applicable path is displayed in a second color.

9. The method according to claim 7, wherein each candidate path is displayed as an intensity profile.

10. The method according to claim 9, wherein the intensity profile is configured to be displayed in association with at least one image of an area around a local intensity extrema of the intensity profile.

11. The method according to claim 1, further comprising an act of determining an acceptance threshold of the information about the local intensity extrema and/or intensity variation for each candidate path of movement by adjacent paths of each candidate path of movement.

12. The method according to claim 1, further comprising an act of calculating the information about the local intensity extrema and/or intensity variation by integrating the intensity data over a maximum cross section of the object perpendicular to a direction of movement along the candidate path of movement.

13. The method according to claim 1, wherein the object is at least one of a surgical device and a diagnostical device.

14. A non-transitory computer-readable medium comprising instructions for determining an applicable path of a movement of an object in a tissue based on intensity data obtained by a 3D imaging technique, the applicable path of movement connecting a starting postion of the object with a defined target location, which, when executed by a processor, configured the processor to perform acts of:
defining the defined target location of a reference point of the object and choosing at least one possible starting postion of the reference point of the object;
determining a candidate path of movement between each position of the at least one possible starting position and the defined target location;
directly after the determining act, evaluating the candidate path of movement as being the applicable path depending on information about local intensity extrema and/or intensity variation resulting from the intensity data along each candidate path of movement, wherein the evaluating act is performed on an unsegmented image of the tissue and forms an output including the applicable path;and
causing a rendering device to render the output on the rendering device.

15. A computerized system comprising a processing unit, a memory, a data interface, a display and an input device, wherein the system is configured to perform the method of claim 1.

16. A system for determining an applicable path of a movement of an object in a tissue based on intensity data obtained by a 3D imaging technique, the applicable path of movement connecting a starting position of the object with a defined target location, the system comprising a computer which is configured to perform acts of:
defining the defined target location of a reference point of the object and choosing at least one possible starting position of the reference point of the object;
determining a candidate path of movement between each position of the at least one possible starting position and the defined target location;
directly after the determining act, evaluating the candidate path of movement as being an applicable path depending on information about local intensity extrema and/or intensity variation resulting from the intensity data along each candidate path of movement, wherein the evaluating act is performed on an unsegmented image of the tissue and forms an output including the applicable path; and
causing a rendering device to render the output on the rendering device.

17. The system of claim 16, wherein the candidate path of movement is a linear path of movement connecting the at least one possible starting position and the target location along a shortest route.

18. The system of claim 16, wherein the rendering device is a display and the causing act causes displaying on the display a region of interest of the at least one possible starting position, wherein the at least one starting position of the applicable path is displayed in a first color and the at least one starting position of each candidate path not being the applicable path is displayed in a second color.

19. The system of claim 16, wherein the rendering device is a display and the causing act causes displaying on the display each candidate path as an intensity profile.

20. The system of claim 19, wherein the intensity profile is configured to be displayed in association with at least one image of an area around a local intensity extrema of the intensity profile.

* * * * *